US012805970B2

(12) United States Patent
Alvarez-Gomez et al.

(10) Patent No.: US 12,805,970 B2
(45) Date of Patent: Nov. 24, 2026

(54) TECHNIQUE FOR PROCESSING MEDICAL IMAGE DATA OF A PATIENT'S BODY

(71) Applicant: Stryker European Operations Limited, Carrigtwohill (IE)

(72) Inventors: Julio C. Alvarez-Gomez, Stegen (DE); Johannes Silberbauer, Freiburg (DE); Patrick Hornecker, Eichstetten (DE)

(73) Assignee: Stryker European Operations Limited, Carrigtwohill (IE)

( * ) Notice: Subject to any disclaimer, the term of this patent is extended or adjusted under 35 U.S.C. 154(b) by 47 days.

(21) Appl. No.: 18/967,878

(22) Filed: Dec. 4, 2024

(65) Prior Publication Data

US 2025/0186160 A1 Jun. 12, 2025

(30) Foreign Application Priority Data

Dec. 7, 2023 (EP) .................................... 23214830

(51) Int. Cl.
*A61B 90/00* (2016.01)
*G06T 7/33* (2017.01)

(52) U.S. Cl.
CPC .............. *A61B 90/37* (2016.02); *G06T 7/337* (2017.01); *A61B 2090/3764* (2016.02); *G06T 2207/10121* (2013.01); *G06T 2207/30012* (2013.01)

(58) Field of Classification Search
CPC ..... G06T 7/0012; G06T 7/0014; G06T 7/337; A61B 90/37; A61B 6/505; A61B 6/02
See application file for complete search history.

(56) References Cited

U.S. PATENT DOCUMENTS

| | | | |
|---|---|---|---|
| 5,951,475 A | 9/1999 | Gueziec et al. | |
| 7,227,564 B2 | 6/2007 | Nakatsu | |

(Continued)

FOREIGN PATENT DOCUMENTS

| | | |
|---|---|---|
| EP | 2690596 B1 | 8/2018 |
| EP | 3306567 B1 | 3/2020 |
| WO | 2021061924 A1 | 4/2021 |

OTHER PUBLICATIONS

Chang, Chih-Ju et al., "Registration of 2D C-Arm and 3D CT Images for a C-Arm Image-Assisted Navigatin System for Spinal Surgery", Applied Bionics and Biomechanics, vol. 2015, Article ID 478062, 2015, 9 pages.

(Continued)

*Primary Examiner* — Carolyn A Pehlke
(74) *Attorney, Agent, or Firm* — Howard & Howard Attorneys PLLC

(57) ABSTRACT

A method, computer program and system for processing medical image data of a patient's body are provided. Medical image data including two 2D images is obtained, each depicting two common anatomical elements of the patient's body from a known viewing direction, the known viewing direction differing between the 2D images. A first spatial pattern indicative of first 3D positions of the common anatomical elements is determined. A second spatial pattern indicative of second 3D positions of a plurality of anatomical elements of the patient's body, said plurality of anatomical elements comprising the two common anatomical elements, is obtained. A mapping is determined between the first spatial pattern and the second spatial pattern to associate at least one of the first three-dimensional positions with at least one of the second three-dimensional positions.

18 Claims, 7 Drawing Sheets

(56) References Cited

U.S. PATENT DOCUMENTS

| | | | |
|---|---|---|---|
| 7,570,791 B2 | 8/2009 | Frank et al. | |
| 7,620,223 B2 | 11/2009 | Xu et al. | |
| 7,940,999 B2 | 5/2011 | Liao et al. | |
| 8,010,177 B2 | 8/2011 | Csavoy et al. | |
| 8,031,922 B2 | 10/2011 | Haimerl et al. | |
| 9,165,362 B2 | 10/2015 | Siewerdsen et al. | |
| 9,240,046 B2 | 1/2016 | Carrell et al. | |
| 9,684,980 B2 | 6/2017 | Royalty et al. | |
| 9,875,544 B2 | 1/2018 | Rai et al. | |
| 10,043,111 B2 | 8/2018 | Akahori | |
| 10,262,424 B2 | 4/2019 | Ketcha et al. | |
| 10,368,956 B2 | 8/2019 | Siewerdsen et al. | |
| 10,405,821 B2 | 9/2019 | Hansis et al. | |
| 10,842,461 B2 | 11/2020 | Johnson et al. | |
| 10,902,587 B2 | 1/2021 | Manickam et al. | |
| 11,284,846 B2 | 3/2022 | Graumann et al. | |
| 11,317,971 B2 | 5/2022 | Crawford | |
| 11,657,518 B2 | 5/2023 | Ketcha et al. | |
| 2021/0251591 A1 | 8/2021 | Johnson | |
| 2022/0265352 A1 | 8/2022 | Zucker | |
| 2022/0287777 A1 | 9/2022 | Crawford | |
| 2022/0392085 A1 | 12/2022 | Finley et al. | |
| 2023/0123621 A1 | 4/2023 | Joshi et al. | |
| 2023/0169645 A1 | 6/2023 | Helm et al. | |
| 2023/0169646 A1 | 6/2023 | Helm et al. | |
| 2023/0169676 A1 | 6/2023 | Helm et al. | |
| 2023/0169753 A1 | 6/2023 | Helm et al. | |
| 2023/0240628 A1* | 8/2023 | Cohen .................. | A61B 6/4441 382/128 |
| 2024/0144498 A1* | 5/2024 | Woo ........................ | A61B 34/25 |

OTHER PUBLICATIONS

Ketcha, M.D. et al., "Multi-Stage 3D-2D Registration for Correction of Anatomical Deformation in Image-Guided Spine Surgery", Physics in Medicine and Biology, Institute of Physics Publishing, Bristonl GB, vol. 62, No. 11, May 11, 2017, pp. 4604-4622.

Mi, Jia et al., "SGReg: Segmentation Guided 3D/2D Rigid Registration for Orthogonal X-Ray and CT Images in Spine Surgery Navigation", vol. 68, No. 13, Jun. 21, 2023, 19 pages.

Otake, Y et al., "Automatic Localization of Vertebral Levels in X-Ray Fluoroscopy Using 3D-2D Registration: A Tool to Reduce Wrong-Site Surgery", Physics in Medicine and Biology, Institute of Physics Publishing, Bristol GB, vol. 57, No. 17, Aug. 3, 2012, pp. 5485-5508.

Zhang, S, An Automatic ICP-Based 2D-3D Registration Method for a High-Speed Biplanar Videoradiography Imaging System, www.int-arch-photogramm-remote-sens-spatial-inf-sci.net/XLIII-B2-2020/805/2020/isprs-archives-XLIII-B2-2-2020-805-2020.pdf, Aug. 12, 2020, 8 pages.

* cited by examiner

TECHNIQUE FOR PROCESSING MEDICAL IMAGE DATA OF A PATIENT'S BODY

PRIORITY CLAIM

This application claims priority to and all the benefits of European Patent Application No. 23214830, filed Dec. 7, 2023, the entire contents of which are hereby incorporated by reference.

TECHNICAL FIELD

The present disclosure provides a method for processing medical image data of a patient's body, a system and a computer program.

BACKGROUND

In various surgical procedures, two-dimensional (2D) medical images of a patient's body are of interest for the surgeon. For example, pre-operative or intra-operative X-ray images may be acquired using a medical image acquisition device such as a so-called C-Arm.

It is generally desired to associate such 2D images and/or information derived therefrom with additional information.

For example, it may be desired to obtain a registration between the two-dimensional images and three-dimensional (3D) medical image data of the patient's body, for example magnetic resonance (MR) image data and/or computed tomography (CT) image data. Known solutions require a surgeon to perform such a registration by aligning the images relative to one another. Other solutions require the determination of digitally rendered radiographs (DRRs) to be aligned relative to the two-dimensional images, which generally requires large processing resources.

As another example, in current solutions, 2D images are not associated with an orientation of the patient during image acquisition, so the surgeon may need to derive anatomical directions from said images by himself. Patient orientation information may also be helpful for later computational image processing steps. For instance, if the images are to be used for surgical navigation, the patient orientation may be considered for generating navigation views of interest for the surgeon.

As a still further example, identities of anatomical elements represented by the images may be of interest for a surgeon and/or for subsequent image processing steps such as surgical planning and/or surgical navigation. Similar to the patient orientation, current solutions require surgeons to derive such identities of anatomical elements by themselves.

SUMMARY

There is a need for a technique that solves one or more of the above or other problems. It may be particularly advantageous to associate positions of anatomical elements shown in 2D images and in 3D image data with one another. In certain examples, this may allow transferring anatomical information such as identities of anatomical elements and/or a patient orientation from one type of image to the other and/or determining a registration between the different types of images.

According to a first aspect, a method for processing medical image data of a patient's body is provided. The method is performed by at least one processor and comprises obtaining medical image data. The medical image data comprises at least two two-dimensional medical images, each depicting, at least, two or more common anatomical elements of the patient's body from a known viewing direction, the known viewing direction differing between the at least two two-dimensional medical images. The method further comprises determining, based on the at least two two-dimensional medical images comprised in the medical image data and based on the known viewing directions, a first spatial pattern indicative of first three-dimensional positions of the two or more common anatomical elements. The method comprises obtaining a second spatial pattern indicative of second three-dimensional positions of a plurality of anatomical elements of the patient's body, said plurality of anatomical elements comprising the two or more common anatomical elements. The method further comprises determining a mapping between the first spatial pattern and the second spatial pattern to associate at least one of the first three-dimensional positions with at least one of the second three-dimensional positions.

The method may be referred to as a computer-implemented method. The method may not comprise a surgical step. The at least two 2D images may comprise or be X-ray images. The two or more common anatomical elements are depicted in each of the at least two 2D image, so these anatomical elements are common among the 2D images, hence the name "common" anatomical element. The two or more common anatomical elements may comprise a bone of the patient's body. Each of the two or more common anatomical elements may correspond to a different bone of the patient's body. The anatomical elements may correspond to vertebrae of the patient's spine. The known viewing direction may be a lateral (LAT) direction or an anterior-posterior (AP) direction. The known viewing direction may be (e.g. pre-) defined relative to the patient's body. The first spatial pattern may consist of the first 3D positions. The second spatial pattern may consist of the second 3D positions. The mapping may be determined using a pattern matching, a point matching and/or a curve matching algorithm. One exemplary algorithm that can be used for determining the mapping is the so-called iterative closest point (ICP) algorithm.

The method may further comprise triggering display of a visualization. The visualization may comprise at least one of the two-dimensional medical images and information that is based on the mapping. The visualization may be output on a display, for example a display of a surgical navigation system. The information that is based on the mapping may comprise an identifier of one or more of the common anatomical elements, a patient orientation, and/or an indication (e.g., an overlay) of (e.g., an outline of) one or more of the common anatomical elements as represented by the 3D image data. The visualization may include a representation of a tracked surgical instrument. In this case, the visualization may be referred to as a navigation view.

For example, the second spatial pattern and/or one or more of the second three-dimensional positions are associated with predefined anatomical information. The method may comprise obtaining said predefined anatomical information (e.g., together with the second spatial pattern). The method may further comprise assigning, based on the determined mapping, at least a part of the predefined anatomical information to one or more of: {a} the associated at least one of the first three-dimensional positions, {b} at least one of the common anatomical elements, {c} one or more of the two-dimensional medical images, {d} the medical image data.

The information that is based on the mapping may comprise an indication of the assigned part of the predefined anatomical information. The visualization may include an indication of the assigned part of the predefined anatomical information.

The predefined anatomical information may comprise at least one predefined identifier or label that is associated with one of the plurality of anatomical elements. In this case, assigning at least a part of the predefined anatomical information may comprise assigning the at least one predefined identifier or label. The identifier or label may be associated with the one of the plurality of anatomical elements by a user or automatically (e.g., by matching the one of the plurality of anatomical elements to an anatomical atlas comprising said identifier or label).

The predefined anatomical information may comprise a patient orientation. In this case, assigning at least a part of the predefined anatomical information may comprise assigning the patient orientation. The patient orientation may be associated with the 3D image data by a user or automatically (e.g., based on metadata comprised in the 3D image data such as a DICOM header).

The method may further comprise determining, for at least one of the common anatomical elements, the first three-dimensional position based on a segmentation of the at least one of the common anatomical elements in one or more of the at least two two-dimensional medical images. Determining the first spatial pattern may comprise determining the first 3D position(s). The method may comprise determining the segmentation of the at least one of the common anatomical elements.

The method may further comprise determining, for at least one of the common anatomical elements, a first outline or bounding box in a first one of the two-dimensional medical images and a second outline or bounding box in a second one of the two-dimensional medical images. The first three-dimensional position of the at least one of the common anatomical elements may be determined based on {i} the first outline or bounding box and {ii} the second outline or bounding box. The first three-dimensional position of the at least one of the common anatomical elements may be determined based on {i} a first projection of the first outline or bounding box (e.g., along the known viewing direction and/or towards a viewing point such as an X-ray origin) associated with the first one of the two-dimensional medical images and {ii} a second projection of the second outline or bounding box (e.g., along the known viewing direction and/or towards a viewing point such as an X-ray origin) associated with the second one of the two-dimensional medical images. The method may comprise determining the first projection and the second projection.

The first three-dimensional position of the at least one of the common anatomical elements may be determined based on a three-dimensional position of a virtual intersection volume of the first projection and the second projection. The method may comprise determining the virtual intersection volume. For example, a three-dimensional position of a center of the virtual intersection volume is used as the first three-dimensional position of the at least one of the common anatomical elements.

The method may comprise determining a 3D position of the center of the virtual intersection volume as the first 3D position.

The second spatial pattern may be determined based on reference image data of at least the plurality of anatomical elements. The method may comprise determining the second spatial pattern based on the reference image data. The reference image data may comprise or be 3D image data, e.g., MR image data and/or CT image data. For example, at least one or each of the second three-dimensional positions is determined based on a segmentation of one of the plurality of anatomical elements as represented by the reference image data. The method may comprise determining the segmentation of the one of the plurality of anatomical elements based on the reference image data to determine the at least one of the second 3D positions. The method may further comprise determining a registration between the medical image data and the reference image data based on the mapping.

The first spatial pattern may comprise a first virtual geometrical object defined by the first three-dimensional positions and the second spatial pattern may comprise a second virtual geometrical object defined by the second three-dimensional positions. Determining the mapping may comprise optimizing an alignment between the first virtual geometrical object and the second virtual geometrical object. Optimizing the alignment may comprise scaling, rotating and/or shifting one or both of the first virtual geometrical object and the second virtual geometrical object. In one example, determining the mapping is determined without deforming (e.g., bending) the respective virtual geometrical object.

The first virtual geometrical object may comprise a first curve modeling (e.g., fitting and/or extending through) the first three-dimensional positions and the second virtual geometrical object may comprise a second curve modeling (e.g., fitting and/or extending through) the second three-dimensional positions. Determining the mapping may comprise matching the first curve to the second curve or matching the second curve to the first curve.

According to a second aspect, a system is provided. The system comprises at least one processor configured to carry out the method according to the first aspect. The at least one processor may be configured to: obtain medical image data comprising at least two two-dimensional medical images, each depicting, at least, two or more common anatomical elements of the patient's body from a known viewing direction, the known viewing direction differing between the at least two two-dimensional medical images; determine, based on the at least two two-dimensional medical images comprised in the medical image data and based on the known viewing directions, a first spatial pattern indicative of first three-dimensional positions of the two or more common anatomical elements; obtain a second spatial pattern indicative of second three-dimensional positions of a plurality of anatomical elements of the patient's body, said plurality of anatomical elements comprising the two or more common anatomical elements; and determine a mapping between the first spatial pattern and the second spatial pattern to associate at least one of the first three-dimensional positions with at least one of the second three-dimensional positions.

The system may further comprise a medical imaging apparatus (e.g., an MR scanner, a CT scanner or a C-arm) configured to acquire the medical image data and/or the reference image data. The system may comprise a feedback unit, such as a display, configured to output a (e.g., the) visualization.

According to a third aspect, a computer program is provided. The computer program stores instructions which, when executed by at least one processor (e.g., the processor of the system according to the second aspect), cause the at least one processor to carry out the method according to the first aspect. The computer program may store instructions which, when executed by the at least one processor, cause the at least one processor to: obtain medical image data comprising at least two two-dimensional medical images, each depicting, at least, two or more common anatomical elements of the patient's body from a known viewing direction, the known viewing direction differing between the at least two two-dimensional medical images; determine, based on the at least two two-dimensional medical images comprised in the medical image data and based on the known viewing directions, a first spatial pattern indicative of first three-dimensional positions of the two or more common anatomical elements; obtain a second spatial pattern indicative of second three-dimensional positions of a plurality of anatomical elements of the patient's body, said plurality of anatomical elements comprising the two or more common anatomical elements; and determine a mapping between the first spatial pattern and the second spatial pattern to associate at least one of the first three-dimensional positions with at least one of the second three-dimensional positions. The computer program may be carried by a carrier (e.g., a data stream) and/or stored on a non-transitory computer-readable storage medium.

SHORT DESCRIPTION OF THE FIGURES

Embodiments and examples in accordance with the present disclosure will now be described with reference to the figures, wherein.

Figure 6A:
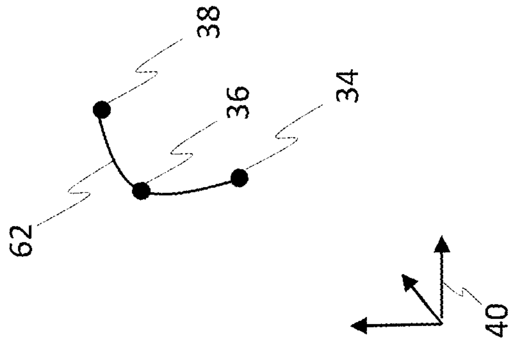
Figure 6B:
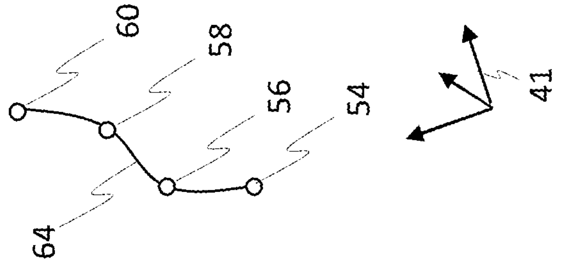
Figure 6C:
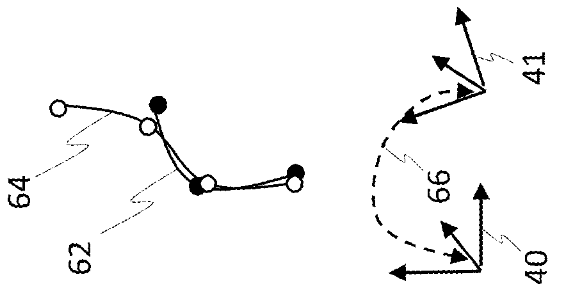
Figure 7:
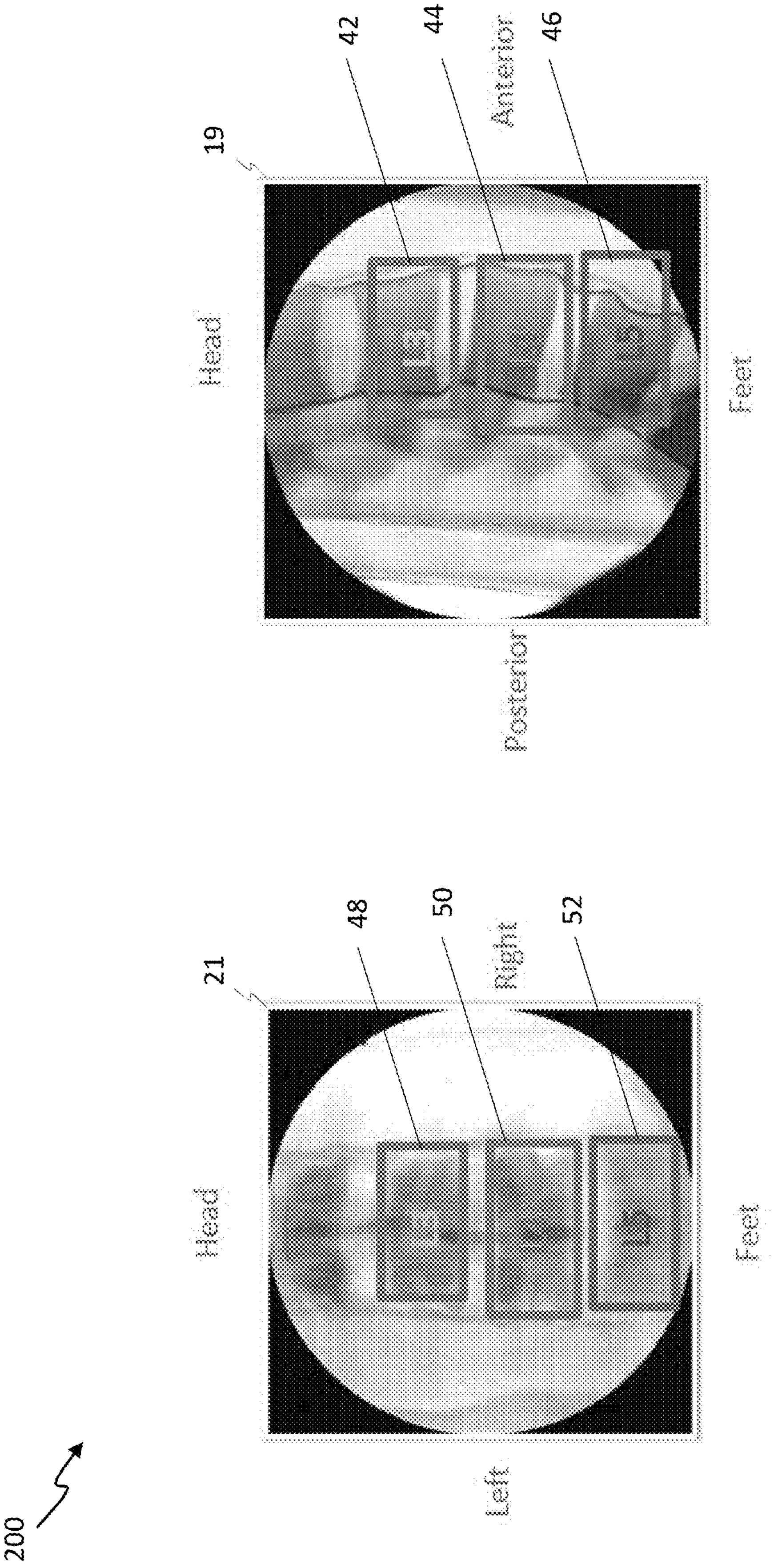

FIG. 6*a* illustrates a first pattern of the first 3D positions;

FIG. 6*b* illustrates a second pattern of the second 3D positions;

FIG. 6*c* illustrates the first and second pattern matched to one another; and FIG. 7 illustrates exemplary visualizations in accordance with the present disclosure.

DETAILED DESCRIPTION

Unless indicated otherwise, reference signs used in the following refer to the same or similar structural or functional features.

Figure 1:
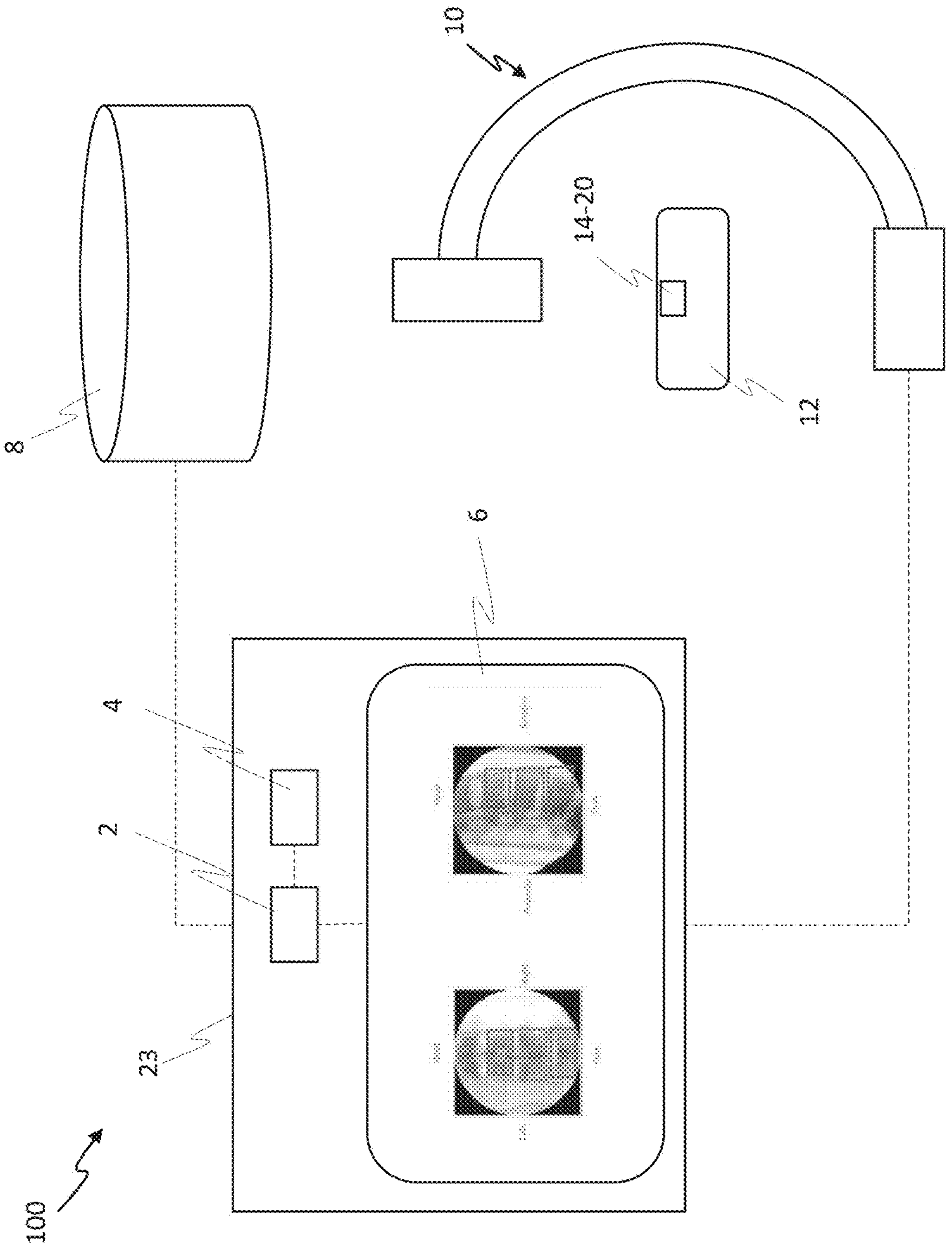
FIG. 1 shows a system in accordance with the present disclosure.

FIG. 1 shows a system 100 in accordance with the present disclosure. The system 100 comprises a processor 2 and a memory 4 storing instructions which, when executed by the processor 2, caused the processor 2 to perform the method disclosed herein. In the illustrated example, the system 100 further comprises a display 6, a database 8 (e.g., a PACS) and a medical image acquisition device in the form of a C-arm 10, each being communicatively connected to the processor 2. The C-arm can be used to (e.g., pre-operatively) acquire a 3D scan of the patient's body 12 comprising vertebrae 14-20, and may also be used to (e.g., intra-operatively) acquire a LAT and an AP fluoroscopy image as 2D images of the body 12. Medical images of the patient may be stored in the database 8. The processor may obtain such medical images either directly from the C-arm 10 or from the database 8. In the latter case, the processor 2 need not be directly connected to the C-arm 10. The processor 2 and/or the memory 4 may be implemented as distributed components, e.g., as virtual network functions of a cloud computing platform. Alternatively, the processor 2 and the memory 4 may be arranged in a navigation system 23 comprising display 6, to be located in an operating room of a hospital.

Figure 2:
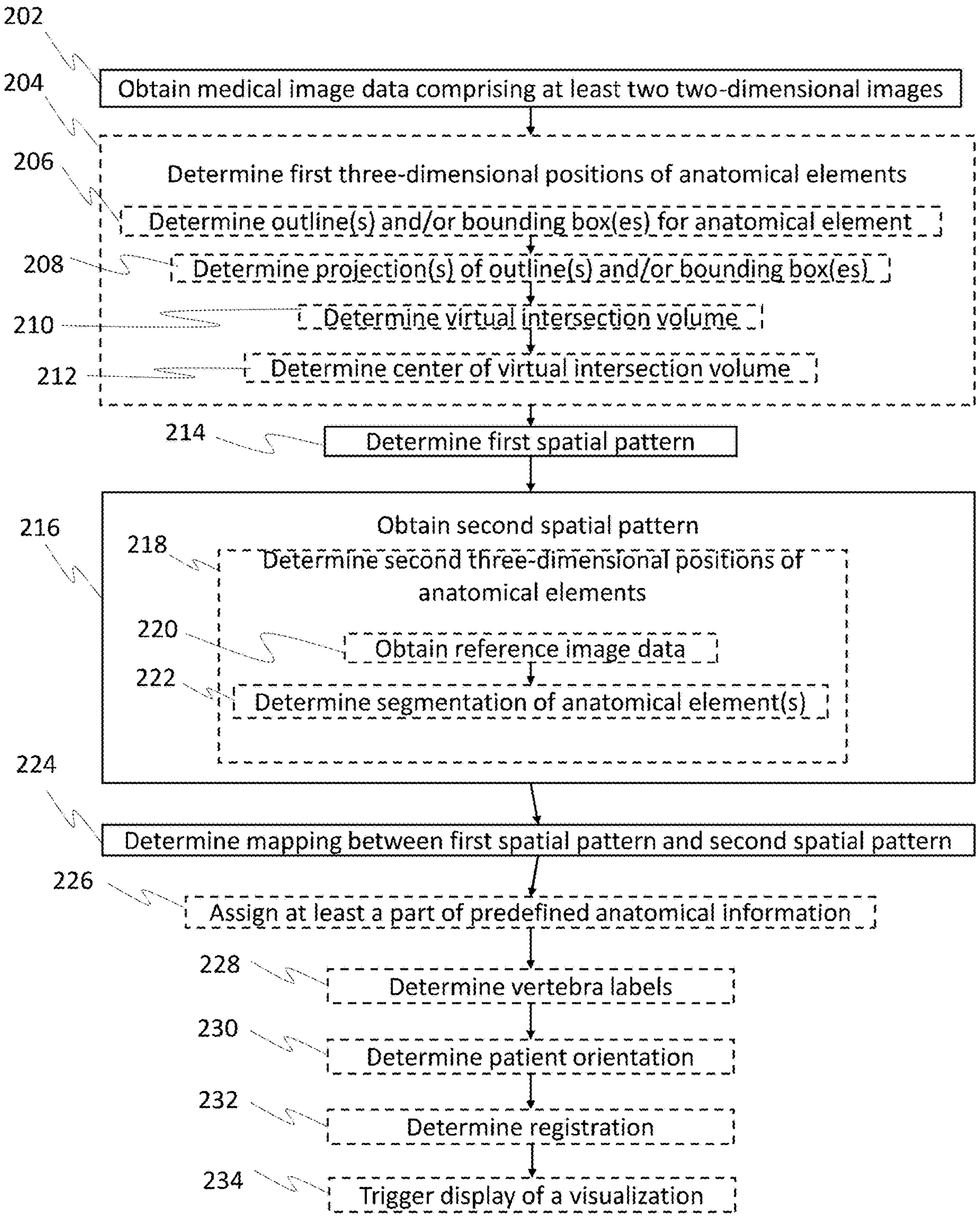
FIG. 2 shows a flowchart of a method in accordance with the present disclosure.

FIG. 2 shows a flowchart of a method in accordance with the present disclosure. This method may be performed by the processor 2.

In step 202, medical image data is obtained. The medical image data may be obtained from the database 8 and/or from a medical image acquisition device such as the C-arm 10. The medical image data comprises at least two two-dimensional medical images of at least a part of the patient's body 12. Each of the 2D images is associated with a known viewing direction of the image acquisition device that was used when acquiring the respective image. These viewing directions may be defined in a spatial coordinate system of an operating room in which the medical imaging apparatus is located and/or relative to the patient's body 12. For example, an AP X-ray image and a LAT X-ray image may be comprised in the medical image data. The medical image data may comprise direction information (e.g., as part of an image's metadata) indicative of the known respective viewing direction. Each of the images depicts at least two anatomical elements of the patient's body. These at least two anatomical elements are thus represented by each of the at least two 2D images and may be referred to as common anatomical elements herein. In the following, the vertebrae 14-20 will be used as specific examples of such anatomical elements, although the present disclosure is not limited thereto (e.g., other bones or organs of the patient's body may be used as common anatomical elements).

Figure 3:
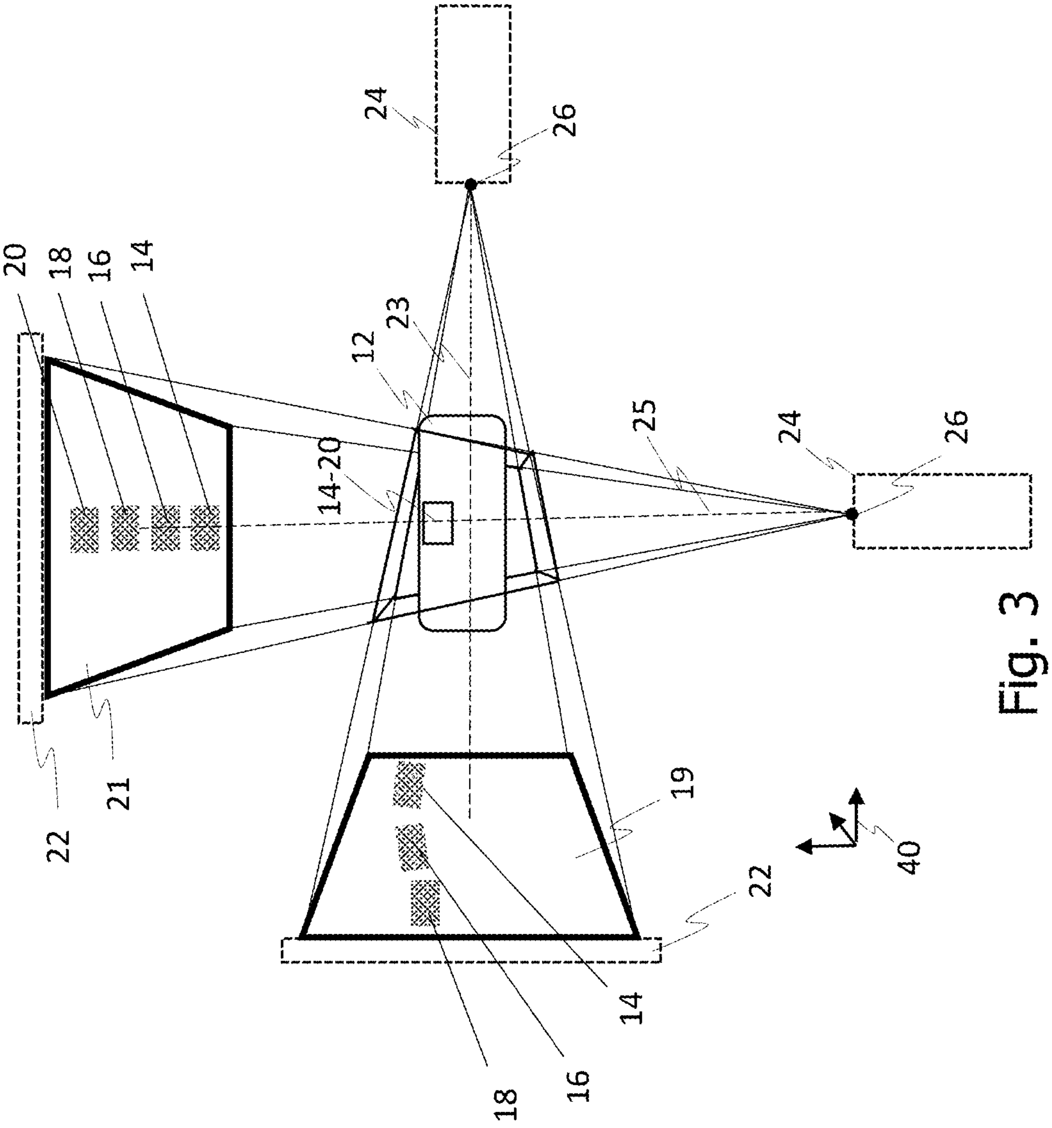
FIG. 3 illustrates two 2D images in accordance with the present disclosure.

FIG. 3 illustrates two 2D images 19, 21 that may be part of the medical image data acquired in step 202. Also shown are poses of an X-ray detector 22 and an X-ray source 24 of the C-arm 10 present when acquiring the respective 2D images. During image acquisition, X-rays are emitted by the source 24 from a viewing point 26 towards the detector 22. The X-rays penetrate the patient's body 12 and impinge on the detector 22 to form the respective image 19, 21 depicting the vertebrae 14-20. Thus, the X-rays forming the 2D images 19, 21 cover a spatial volume in the form of a pyramid or cone, having an associated viewing axis 23, 25 of the C-arm 10 as a central axis. In the example of FIG. 1, the 2D image 19 is a LAT image of the patient's body 12, whereas the 2D image 21 is an AP image thereof. It is to be understood that other viewing directions are also possible (e.g., offset from one another by less than 90°, offset from one another by more than 90°, outside one or more of the anatomical planes of the patient's body and/or intersecting one or more of the anatomical planes of the patient's body).

In optional step 204, first 3D positions of one or more anatomical elements depicted in the 2D images are determined. For example, first 3D positions are determined for each common anatomical element based on the medical image data, in particular based on the 2D images (e.g., segmentations of the common anatomical elements in these images) and the known viewing directions thereof.

As indicated in FIG. 2, step 204 may comprise sub-step 206, in which (e.g., rectangular) bounding boxes and/or outlines of the common anatomical elements are determined (e.g., based on the segmentations of the common anatomical elements or as part of segmenting the common anatomical elements) in each of the 2D images. The first 3D positions may then be determined based on the bounding boxes and/or outlines in the 2D images and based on the known viewing directions thereof.

In optional sub-step 208, for each of the bounding boxes and/or outlines, a respective projection in the viewing direction of the 2D image is determined. The projection may be a linear projection along a viewing axis (e.g., the axis 23 or 25) or a projection towards a particular 3D position (e.g., the 3D position of the viewing point 26). The known viewing direction may be indicative or include the viewing axis and/or the viewing point (e.g., a point at which X-rays of the medical imaging device originate). The first 3D positions may be determined based on these projections.

In optional sub-step 210, a virtual intersection volume is determined between a first projection of a bounding box or contour of a common anatomical element in a first of the 2D images and a second projection of a bounding box or contour of the same common anatomical element in a second of the 2D images. Such a virtual intersection volume may be determined for each of the common anatomical elements, wherein each intersection volume is associated with exactly one common anatomical element.

The first 3D positions may be determined based on the virtual intersection volumes.

In optional sub-step 212, centers of the virtual intersection volumes are determined. The first 3D positions of these centers may then be used as the first 3D positions of the common anatomical elements.

Figure 4:
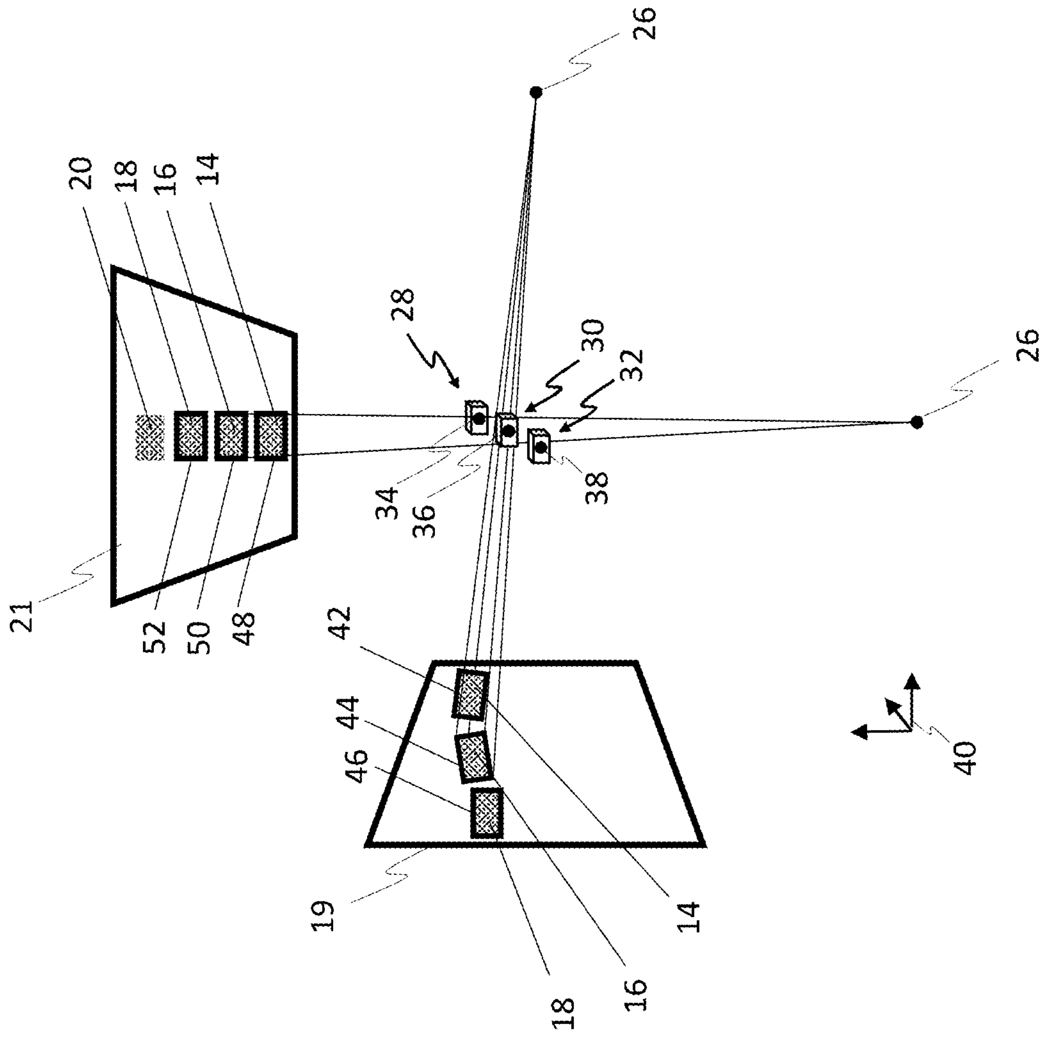
FIG. 4 illustrates virtual intersection volumes and first 3D positions determined based on the 2D images of FIG. 3.

FIG. 4 illustrates virtual intersection volumes 28-32 and first 3D positions 34-38 determined in coordinate system 40 based on the 2D images of FIG. 3. Rectangular bounding boxes 42-46 of vertebrae 14-18 depicted in image 19 are determined using a segmentation algorithm. Similarly, rectangular bounding boxes 48-52 of the same vertebrae 14-18 as common anatomical elements are determined in image 21. The bounding boxes approximate an outer contour of the respective vertebrae. Alternatively to using bounding boxes, the (e.g., non-rectangular) outline of a vertebra as detected in the image 19, 21 may be used. These bounding boxes or outlines are then virtually projected in space toward the viewing point 26 indicated by the known viewing direction of the respective image 19, 21. The intersection of these projection volumes of a common anatomical element forms a virtual intersection volume for said common anatomical element. Each virtual intersection volume 28-32 has a center, the 3D position of which in the coordinate system 40 can be used as the first 3D position of the common anatomical element associated with said virtual intersection volume 28-32. One may say that the known viewing directions, which are different for the at least two 2D images, are used to approximate, for each common anatomical element, a region in the coordinate system 40 in which the common anatomical element is assumed to have been located during acquisition of the images 19, 21. In this manner, a first 3D position and optionally a first 3D pose of the common anatomical element can be derived from multiple 2D images.

In step 214, a first spatial pattern is determined based on the at least two two-dimensional medical images comprised in the medical image data and based on the known viewing directions. The first spatial pattern is indicative of first three-dimensional positions of the two or more common anatomical elements. The first spatial pattern may consist of the first 3D positions determined for the common anatomical elements.

In step 216, a second spatial pattern is obtained. The second spatial pattern is indicative of second 3D positions of a plurality of anatomical elements of the patient's body 12, said plurality of anatomical elements comprising the two or more common anatomical elements. Referring to the example of FIGS. 3 and 4, the second spatial pattern may be indicative of second 3D positions of the vertebrae 14-20. The second spatial pattern may be associated with 3D medical image data of the patient's body such as a CT scan or an MR scan of the patient's body 12.

In case the second 3D positions are not known in advance, the method may comprise optional step 218 in which the second 3D positions are determined. Step 218 may comprise sub-step 220 in which reference image data of the patient's body 12 is obtained. The reference image data may comprise one or more 3D medical images of the patient's body, e.g. a CT scan and/or an MR scan. In optional sub-step 222, the anatomical elements (e.g., at least the common anatomical elements) are segmented in the reference image data. A position of a center of a so-segmented anatomical element may then be used as the second 3D position of said anatomical element.

Figure 5:
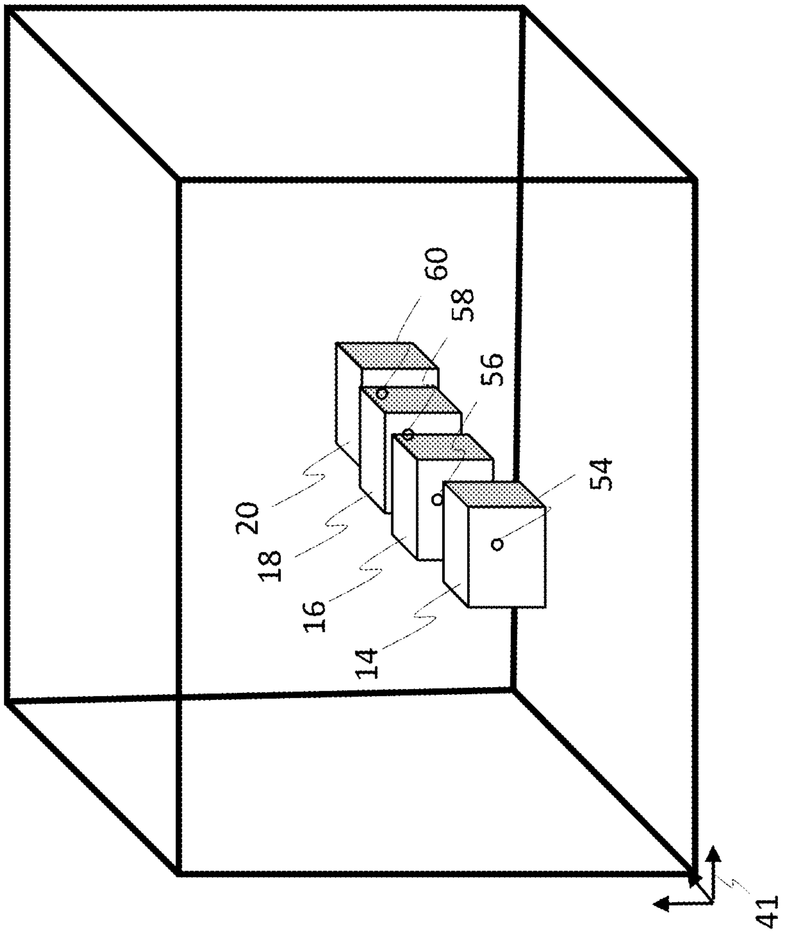
FIG. 5 illustrates reference image data and second 3D positions.

FIG. 5 illustrates reference image data and second 3D positions 54-60 of the vertebrae 14-20 determined based thereon. The reference image data is associated with a coordinate system 41 in which the second 3D positions are defined. The coordinate system 41 may be defined in a (e.g., DICOM) header of the reference image data.

In step 224, a mapping is determined between the first and the second spatial pattern to associate the first 3D positions with the second 3D positions. The mapping may comprise a transformation (e.g., a translation and/or rotation and/or homogeneous scaling in all spatial directions) between the first and the second spatial pattern. The mapping may define a (e.g., coordinate) transformation between the coordinate systems 40 and 41 that is to be used to match the first to the second spatial pattern or vice versa.

FIG. 6*a* illustrates an exemplary first pattern of the first 3D positions in the coordinate system 40. FIG. 6*b* illustrates an exemplary second pattern of the second 3D positions in the coordinate system 41. It can be seen that each pattern comprises a virtual geometrical object which, in the illustrated examples, comprises a curve 62, 64. FIG. 6*c* illustrates the first and second pattern matched to one another: Determining the mapping may comprise performing a pattern matching between the first and second pattern and/or performing a curve matching between the two curves 62, 64. The mapping may be indicative of a transformation 66 between the two coordinate systems 40, 41.

With the mapping determined, the method may proceed with one or more of optional steps 226-234.

The second spatial pattern and/or one or more of the second 3D positions may be associated with predefined anatomical information. The predefined anatomical information may be indicative of an identifier of the common anatomical element(s) and/or anatomical directions of the patient's body 12 (e.g., in the coordinate system 41). In optional step 226, at least a part of said predefined anatomical information is assigned directly to the associated first 3D position(s) or assigned to the common anatomical element having the associated first 3D position. In this manner, the part of the predefined anatomical information can be transferred from the 3D space into the 2D image space. Put differently, the 2D images can be enriched with the predefined anatomical information based on the determined mapping.

In optional step 228, vertebra labels are determined for the vertebrae 14-18 as the common anatomical elements. For example, each of the vertebrae 14-20 in the reference image data may be associated with a predefined label (e.g., determined as part of the method or pre-set by a user). The label of a vertebra having a given second 3D position may then be assigned to the vertebra depicted in the 2D images having a first 3D position mapped to said given second 3D position. In other words, the labels of the anatomical elements of the 3D image data may be transferred onto the anatomical elements in the 2D images. For example, each of the bounding boxes in the 2D images may be assigned such a label.

In optional step 230, a patient orientation is determined. The patient orientation may be determined based on the assigned labels. In particular, the labels may be indicative of an anatomical direction or plane of the patient's body 12, so the assigned labels may enable determining said anatomical direction or plane. The patient orientation can then be determined based on the anatomical direction or plane. As another example, the patient orientation may be determined based on a predefined patient orientation that is associated with the second spatial pattern and/or the reference image data. For example, a DICOM header of the reference image data may indicate anatomical direction(s) and/or anatomical plane(s) of the patient relative to the coordinate system 41. These direction(s) and/or plane(s) may then be transferred into the coordinate system 40 based on the transformation 66 to enrich the 2D images with the patient orientation information.

In optional step 232, a registration between the 2D images and the reference image data is determined. For example, the transformation 66 is used as the registration. The registration may be used for transforming positions from one of the coordinate systems 40, 41 into the other and vice versa.

In optional step 234, a visualization is triggered to be output. The visualization comprises one or more (e.g., at least two) of the 2D images, and further comprises information that is based on the mapping. The information that is based on the mapping may comprise the assigned anatomical information (e.g., label(s) and/or patient orientation). The information that is based on the mapping may comprise an indication of (e.g., an outline of) a common anatomical element as represented by the reference image data. The information that is based on the mapping may be displayed as overlay onto the 2D image(s).

FIG. 7 illustrates an exemplary visualization 200 in accordance with the present disclosure, which may be triggered to be displayed on the display 6 in step 234. As can be seen, the visualizations each comprise one of the 2D images as well as an indication of the bounding boxes of the vertebrae 14-18 and the labels "L3", "L4" and "L5" of these common anatomical elements. As can be seen, the image 19 is oriented differently compared with FIG. 4 based on the patient orientation information. The indication of the patient orientation information (Head/Feet/Posterior/Anterior/Left/Right) may not be visualized as such, but may be used for orienting the image to be displayed in accordance with a surgeon's preference.

With the technique disclosed herein, 2D fluoroscopy images can be enhanced with information such as vertebra names and patient orientation. The so-enriched 2D images set the foundation for various use cases, e.g., automatic orientation alignment of navigated 2D and 3D information. This may also yield useful information for enhancing existing workflows, and may reduce the time needed for a procedure since anatomically relevant information can be shown directly on the display during navigation.

Various modifications of the technique disclosed herein are possible. For instance, instead or in addition to vertebrae, the common anatomical elements may comprise other bones or organs of the patient's body 12. Additional variations and advantages of the technique disclosed herein will be apparent to those skilled in the art.

The invention claimed is:

1. A method for processing medical image data of a patient's body, the method being performed by at least one processor and comprising:

obtaining medical image data comprising at least two two-dimensional medical images, each depicting, at least, two or more common anatomical elements of the patient's body from a known viewing direction, the known viewing direction differing between the at least two two-dimensional medical images;

determining, based on the at least two two-dimensional medical images comprised in the medical image data and based on the known viewing directions, a first spatial pattern indicative of first three-dimensional positions of the two or more common anatomical elements;

obtaining a second spatial pattern indicative of second three-dimensional positions of a plurality of anatomical elements of the patient's body, said plurality of anatomical elements comprising the two or more common anatomical elements, wherein the second spatial pattern and/or one or more of the second three-dimensional positions are associated with predefined anatomical information;

determining a mapping between the first spatial pattern and the second spatial pattern to associate at least one of the first three-dimensional positions with at least one of the second three-dimensional positions; and assigning, based on the determined mapping, at least a part of the predefined anatomical information to one or more of: {a} the associated at least one of the first three-dimensional positions, {b} at least one of the common anatomical elements, {c} one or more of the two-dimensional medical images, {d} the medical image data, wherein the predefined anatomical information comprises a patient orientation, and wherein assigning at least a part of the predefined anatomical information further comprises assigning the patient orientation.

2. The method of claim 1, further comprising triggering display of a visualization comprising at least one of the two-dimensional medical images and information that is based on the mapping.

3. The method of claim 1, further comprising triggering display of a visualization comprising at least one of the two-dimensional medical images and information that is based on the mapping, wherein the information that is based on the mapping comprises an indication of the assigned part of the predefined anatomical information.

4. The method of claim 1, wherein the predefined anatomical information comprises at least one predefined label that is associated with one of the plurality of anatomical elements, and wherein assigning at least a part of the predefined anatomical information comprises assigning the at least one predefined label.

5. The method of claim 1, further comprising determining, for at least one of the common anatomical elements, the first three-dimensional position based on a segmentation of the at least one of the common anatomical elements in one or more of the at least two two-dimensional medical images.

6. The method of claim 1, further comprising:

determining, for at least one of the common anatomical elements, a first outline or bounding box in a first one of the two-dimensional medical images and a second outline or bounding box in a second one of the two-dimensional medical images, wherein the first three-dimensional position of the at least one of the common anatomical elements is determined based on {i} the first outline or bounding box and {ii} the second outline or bounding box.

7. The method of claim 6, wherein the first three-dimensional position of the at least one of the common anatomical elements is determined based on {i} a first projection of the first outline or bounding box associated with the first one of the two-dimensional medical images and {ii} a second projection of the second outline or bounding box associated with the second one of the two-dimensional medical images.

8. The method of claim 7, wherein the first three-dimensional position of the at least one of the common anatomical elements is determined based on a three-dimensional position of a virtual intersection volume of the first projection and the second projection.

9. The method of claim 8, wherein a three-dimensional position of a center of the virtual intersection volume is used as the first three-dimensional position of the at least one of the common anatomical elements.

10. The method of claim 1, wherein the second spatial pattern is determined based on reference image data of at least the plurality of anatomical elements.

11. The method of claim 10, wherein at least one or each of the second three-dimensional positions is determined based on a segmentation of one of the plurality of anatomical elements as represented by the reference image data.

12. The method of claim 10, further comprising determining a registration between the medical image data and the reference image data based on the mapping.

13. The method of claim 1, wherein the first spatial pattern comprises a first virtual geometrical object defined by the first three-dimensional positions and the second spatial pattern comprises a second virtual geometrical object defined by the second three-dimensional positions.

14. The method of claim 13, wherein the first virtual geometrical object comprises a first curve modeling the first three-dimensional positions and the second virtual geometrical object comprises a second curve modeling the second three-dimensional positions.

15. The method of claim 1, wherein the anatomical elements correspond to vertebrae of the patient's spine.

16. A system for processing medical image data of a patient's body, the system comprising at least one processor configured to:

obtain medical image data comprising at least two two-dimensional medical images, each depicting, at least, two or more common anatomical elements of the patient's body from a known viewing direction, the known viewing direction differing between the at least two two-dimensional medical images;

determine, based on the at least two two-dimensional medical images comprised in the medical image data and based on the known viewing directions, a first spatial pattern indicative of first three-dimensional positions of the two or more common anatomical elements;

obtain a second spatial pattern indicative of second three-dimensional positions of a plurality of anatomical elements of the patient's body, said plurality of anatomical elements comprising the two or more common anatomical elements, wherein the second spatial pattern and/or one or more of the second three-dimensional positions are associated with predefined anatomical information;

determine a mapping between the first spatial pattern and the second spatial pattern to associate at least one of the first three-dimensional positions with at least one of the second three-dimensional positions; and assigning, based on the determined mapping, at least a part of the predefined anatomical information to one or more of: {a} the associated at least one of the first three-dimensional positions, {b} at least one of the common anatomical elements, {c} one or more of the two-dimensional medical images, {d} the medical image data, wherein the predefined anatomical information comprises a patient orientation, and wherein assigning at least a part of the predefined anatomical information comprises assigning the patient orientation.

17. The system of claim 16, further comprising at least one of the following entities:

i) a medical imaging apparatus configured to acquire the medical image data and/or reference image data; and ii) a feedback unit, such as a display, configured to output a visualization.

18. A non-transitory computer-readable storage medium storing a computer program comprising instructions which, when executed by at least one processor, cause the at least one processor to:

obtain medical image data comprising at least two two-dimensional medical images, each depicting, at least, two or more common anatomical elements of a patient's body from a known viewing direction, the known viewing direction differing between the at least two two-dimensional medical images;

determine, based on the at least two two-dimensional medical images comprised in the medical image data and based on the known viewing directions, a first spatial pattern indicative of first three-dimensional positions of the two or more common anatomical elements;

obtain a second spatial pattern indicative of second three-dimensional positions of a plurality of anatomical elements of the patient's body, said plurality of anatomical elements comprising the two or more common anatomical elements, the second spatial pattern and/or one or more of the second three-dimensional positions are associated with predefined anatomical information;

determine a mapping between the first spatial pattern and the second spatial pattern to associate at least one of the first three-dimensional positions with at least one of the second three-dimensional positions; and assigning, based on the determined mapping, at least a part of the predefined anatomical information to one or more of: {a} the associated at least one of the first three-dimensional positions, {b} at least one of the common anatomical elements, {c} one or more of the two-dimensional medical images, {d} the medical image data, wherein the predefined anatomical information comprises a patient orientation, and wherein assigning at least a part of the predefined anatomical information comprises assigning the patient orientation.

* * * * *